United States Patent
Ressemann et al.

(10) Patent No.: US 6,224,609 B1
(45) Date of Patent: May 1, 2001

(54) BIFURCATED PROSTHETIC GRAFT

(75) Inventors: Thomas V. Ressemann, St. Cloud; Timothy B. Petrick, Brooklyn Park, both of MN (US)

(73) Assignee: Teramed Inc., Maple Grove, MN (US)

( * ) Notice: Subject to any disclaimer, the term of this patent is extended or adjusted under 35 U.S.C. 154(b) by 0 days.

(21) Appl. No.: 09/039,779

(22) Filed: Mar. 16, 1998

(51) Int. Cl.[7] .............................. A61M 29/00; A61F 2/06

(52) U.S. Cl. .................... 606/108; 606/104; 623/1.23

(58) Field of Search .................... 623/1.23, 1.11; 606/191, 198, 194, 195, 108; 604/95

(56) References Cited

U.S. PATENT DOCUMENTS

| | | |
|---|---|---|
| 3,657,744 | 4/1972 | Ersek . |
| 4,140,126 | 2/1979 | Choudhury . |
| 4,503,569 | 3/1985 | Dotter . |
| 4,512,338 | 4/1985 | Balko et al. . |
| 4,577,631 | * 3/1986 | Kreamer ............................ 128/334 |
| 4,617,932 | 10/1986 | Kornberg . |
| 4,655,771 | 4/1987 | Wallsten . |
| 4,665,906 | 5/1987 | Jervis . |
| 4,733,665 | 3/1988 | Palmaz . |
| 4,739,762 | 4/1988 | Palmaz . |
| 4,787,899 | 11/1988 | Lazarus . |
| 4,878,906 | 11/1989 | Lindemann et al. . |
| 4,994,071 | 2/1991 | MacGregor . |
| 5,067,957 | 11/1991 | Jervis . |
| 5,078,726 | 1/1992 | Kreamer . |
| 5,104,399 | 4/1992 | Lazarus . |
| 5,122,154 | 6/1992 | Rhodes . |
| 5,190,546 | 3/1993 | Jervis . |
| 5,275,622 | 1/1994 | Lazarus et al. . |
| 5,290,295 | * 3/1994 | Querals et al. ...................... 606/108 |
| 5,316,023 | 5/1994 | Palmaz et al. . |
| 5,360,443 | 11/1994 | Barone et al. . |
| 5,387,235 | 2/1995 | Chuter . |
| 5,397,355 | 3/1995 | Marin et al. . |
| 5,405,378 | 4/1995 | Strecker . |
| 5,443,477 | 8/1995 | Marin et al. . |
| 5,456,694 | 10/1995 | Marin et al. . |
| 5,456,713 | * 10/1995 | Chuter ............................... 623/1.11 |
| 5,489,295 | 2/1996 | Piplani et al. . |

(List continued on next page.)

FOREIGN PATENT DOCUMENTS

| | | |
|---|---|---|
| 95/08966 | 6/1995 | (WO) . |
| 97/17910 | 5/1997 | (WO) . |

OTHER PUBLICATIONS

Cragg, M.D. et al., "Nonsurgical Placement of Arterial Endoprosthesis: A New Technique Using Nitinol Wire[1]", Radiology, 147:261–263, Apr. 1983.

Dotter, M.D. et al., "Transluminal Expandable Nitinol Coil Stent Grafting: Preliminary Report[1]", Radiology, 147:259–260, Apr. 1983.

Circulation Nov. 1999; 100:19 II–316 "Aortic Arch Reconstruction by Transluminally Plqaced Endovascular Branched Stent Graft" Kanji Inoue, M.D., et al.

J Thoracic and Cardiovascular Surg 1997; 114:5 859–61 "Transluminal Endovascular Branched Graft Placement for a Pseudoaneurysm: Reconstruction of the Descending Thoracic Aorta Including the Celiac Axis" Kanji Inoue, M.D., et al.

(List continued on next page.)

Primary Examiner—David H. Willse
Assistant Examiner—Suzette J. Jackson
(74) Attorney, Agent, or Firm—Popovich & Wiles, P.A.

(57) ABSTRACT

A prosthetic graft for use with a graft system is used to repair the treatment of aortic aneurysms which extend into at least one common iliac artery and do not have a suitable region for seating a stent or other attachment device. The graft is designed to be used in combination with a graft system having legs extending into the common iliac arteries and provides the graft system with a place to securely seat its iliac legs without blocking the internal iliac artery.

15 Claims, 10 Drawing Sheets

U.S. PATENT DOCUMENTS

| | | |
|---|---|---|
| 5,507,769 | 4/1996 | Marin et al. . |
| 5,540,712 | 7/1996 | Kleshinski et al. . |
| 5,540,713 | 7/1996 | Schnepp-Pesch et al. . |
| 5,545,209 * | 8/1996 | Roberts et al. .............. 623/1.11 |
| 5,562,726 * | 10/1996 | Chuter ........................... 623/1.35 |
| 5,569,296 | 10/1996 | Marin et al. . |
| 5,578,071 | 11/1996 | Parodi . |
| 5,578,072 | 11/1996 | Barone et al. . |
| 5,591,196 | 1/1997 | Marin et al. . |
| 5,591,228 | 1/1997 | Edoga . |
| 5,609,627 | 3/1997 | Goicoechea et al. . |
| 5,653,743 * | 8/1997 | Martin ............................ 623/1.35 |
| 5,669,925 * | 9/1997 | Saunders ......................... 606/108 |
| 5,683,449 | 11/1997 | Marcade . |
| 5,683,452 | 11/1997 | Barone . |
| 5,683,453 | 11/1997 | Palmaz . |
| 5,693,083 | 12/1997 | Baker et al. . |
| 5,693,084 | 12/1997 | Chuter . |
| 5,693,087 | 12/1997 | Parodi . |
| 5,723,004 | 3/1998 | Dereume et al. . |
| 5,755,773 | 5/1998 | Evans et al. . |
| 5,755,778 | 5/1998 | Kleshinski . |
| 5,776,186 * | 7/1998 | Uflacker ......................... 623/1.11 |
| 5,824,039 | 10/1998 | Piplani et al. . |
| 5,824,044 | 10/1998 | Quiachon et al. . |
| 5,855,598 | 1/1999 | Pinchuk . |
| 6,039,749 * | 3/2000 | Marin et al. .................... 606/198 |
| 6,039,758 * | 3/2000 | Quiachon et al. ............... 623/1.35 |
| 6,074,362 * | 6/2000 | Jang et al. ...................... 604/104 |
| 6,078,832 * | 6/2000 | Lenker et al. ................... 600/433 |
| 6,129,756 * | 10/2000 | Kugler et al. ................... 623/1.27 |

OTHER PUBLICATIONS

J Endovascular Surg 1997; 4:195–202 "What are the Characteristics of the Ideal Endovascular Graft for Abdominal Aortic Aneurysm Exclusion?" Robert C. Allen, M.D., et al.
Poster presentation from Tenth Annual TCT, Oct. 6–11, 1998, #98, "Endovascular Repair of Aortoiliac Aneurysms Involving Hypogastric Arteries With Branched Stent–Grafts" Tomoyuki Iwase, et al. (32 pages).
PCT Search Report for PCT/US99/06157 (2 pages), references in PCT Search Pgs. (6).

* cited by examiner

BIFURCATED PROSTHETIC GRAFT

FIELD OF THE INVENTION

This invention relates to a bifurcated prosthetic graft and a method for deploying the graft at an area of vessel bifurcation. The invention is a bifurcated prosthetic graft for deployment at the bifurcation of the common iliac artery, and in particular, for use with a biluminal graft system for use in repairing abdominal aortic aneurysms.

BACKGROUND OF THE INVENTION

Aortic aneurysms represent a significant medical problem for the general population. Aneurysms within the aorta presently affect between two and seven percent of the general population and the rate of incidence appears to be increasing. This form of vascular disease is characterized by a degradation in the arterial wall in which the wall weakens and balloons outward by thinning. If untreated, the aneurysm can rupture resulting in death within a short time.

The traditional treatment for patients with an abdominal aortic aneurysm is surgical repair. This is an extensive operation involving transperitoneal or retroperitoneal dissection of the aorta and replacement of the aneurysm with an artificial artery known as a prosthetic graft. This procedure requires exposure of the aorta through an abdominal incision extending from the lower border from the breast bone down to the pubic bone. The aorta is clamped both above and below the aneurysm so that the aneurysm can be opened and the prosthetic graft of approximately the same size as the aorta can be sutured in place. Blood flow is then re-established through the prosthetic graft. The operation requires a general anesthesia with a breathing tube, extensive intensive care unit monitoring in the immediate post-operative period along with blood transfusions and stomach and bladder tubes. All of this imposes stress on the cardiovascular system. This is a high-risk surgical procedure with well-recognized morbidity and mortality.

More recently, significantly less invasive clinical approaches to aneurysm repair known as endovascular grafting have been proposed. (See, Parodi, J. C., et al. "Transfemoral Intraluminal Graft Implantation for Abdominal Aortic Aneurysms," 5 Annals of Vascular Surgery, 491 (1991)). Endovascular grafting involves the transluminal placement of a prosthetic arterial graft in the endoluminal position (within the lumen of the artery). By this method, the graft is attached to the internal surface of an arterial wall by means of attachment devices such as expandable stents, one above the aneurysm and a second below the aneurysm.

It is not uncommon for abdominal aortic aneurysms to extend to the aortic bifurcation or even into the common iliac arteries. When the aneurysm extends into the common iliac arteries it is necessary that the graft system used to repair the aneurysm extend into the common iliac arteries past the aneurysm. This requires that there be enough space between the aneurysm and the common iliac bifurcation so that the graft can properly seat. By "seating" it is meant that the graft is somehow fixed to the non-aneurysmal vasculature. However, in a significant number of patients the aneurysm extends into the common iliac arteries on one or both sides such that there is not enough room to seat the graft without at least partially blocking the internal iliac artery. Such a situation occurs in so-called Class D or E aneurysms. The internal iliac artery is a significant vessel which supplies blood to the pelvic region. Blockage of the vessel can result in undesirable consequences for the patient. For this reason, patients in this category are often excluded from the less expensive and less traumatic endovascular repair and must instead undergo the invasive surgical procedure described above.

Therefore, a need exists for an improved prosthetic graft which will allow endoluminal reconstruction of the common, external, and internal iliac bifurcation. The preferred construction will allow a bifurcated or biluminal aortic graft system to be implanted prior to or following the reconstruction of the iliac bifurcation, while maintaining blood flow to the internal iliac arteries.

SUMMARY OF THE INVENTION

In one aspect, this invention is a prosthetic graft for placement by a single delivery catheter at the bifurcation of a first vessel into second and third vessels within the vasculature of a patient comprising a first graft conduit having first and second ends and first and second stents, the first stent adapted to secure the first end of the first graft conduit within the lumen of the first vessel, the second stent adapted to secure the second end of the first graft conduit within the lumen of the second vessel; and a second graft conduit attached in fluid communication with the first graft conduit, the second graft conduit having a third stent adapted to secure it within the lumen of the third vessel, the first and second graft conduits being sized and configured to be contained within and delivered by the single delivery catheter. Preferably, the first graft conduit forms a first lumen which contains the first and second stents and the second graft conduit forms a second lumen which contains the third stent. The cross-sectional area of the first end of the first graft conduit may be greater than the cross-sectional area of the second end of the first graft conduit. The first and second graft conduits preferably are configured to expand from a first delivery configuration to a second deployed configuration. The cross-sectional area of the first end of the first graft conduit preferably is at least as great as the cross-sectional area of the prosthetic graft at any localized point along a longitudinal axis of the first graft conduit when in the delivery configuration.

In a second aspect, this invention is a method for placing a prosthetic graft in a vessel of a patient's vascular system. The prosthetic graft has a first tubular graft component and a second tubular graft component in fluid communication with it. The method comprises providing a delivery catheter containing the prosthetic graft in a first delivery configuration, the catheter having an angular control element for adjustably controlling the angle between the first and second tubular graft components; advancing the catheter through the vessel to a desired location; manipulating the angular control element to select a desired angle between the first and second tubular graft components; and deploying the prosthetic graft in the vessel in a second expanded configuration. The angular control element of the catheter may include a wire with a pre-formed angle and the step of manipulating the angular control element to select a desired angle may include advancing or retracting the wire. The first tubular graft component may include a first stent attached thereto and the second tubular graft component may include a second stent attached thereto. Preferably, the method further comprises securing the first and second tubular graft components within the vessel by radially expanding the first and second stents.

In a third aspect, this invention is a prosthetic graft for placement by a single delivery catheter at the bifurcation of a first vessel into second and third vessels within the vasculature of a patient comprising a first graft conduit having first and second ends and including a tubular graft component defining a lumen and at least one stent located within the lumen and attached to the graft component, the stent adapted to secure the first end of the first graft conduit within the lumen of the first vessel and the second end of the first graft conduit within the lumen of the second vessel; and a second graft conduit attached in fluid communication with the first graft conduit, the second graft conduit including a tubular graft component defining a lumen and a stent located within the lumen and attached to the graft component and adapted to secure the second graft component within the lumen of the third vessel, the first and second graft conduits being sized and configured to be contained within and delivered by the single delivery catheter.

In a fourth aspect, this invention is a prosthetic graft for placement by a single delivery catheter at the bifurcation of a first vessel into second and third vessels within the vasculature of a patient comprising: a first leg having first and second leg segments, the first leg segment adapted to be deployed in the lumen of the first vessel, the second leg segment adapted to be deployed in the lumen of the second vessel; and a second leg adapted to be deployed in the lumen of the third vessel, whereby the first and second segments of the first leg and the second leg are adapted to be independently deployable within the lumens of the first, second, and third vessels, the first and second legs being sized and configured to be contained within and delivered by the single delivery catheter. The first leg may include a graft component and at least one stent attached to the graft component and the second leg may include a graft component and a stent attached to the second leg graft component.

In a fifth aspect, this invention is a method of placing a prosthetic graft at the bifurcation of the common iliac artery into the external and internal iliac arteries, the prosthetic graft having a first graft conduit with first and second ends and a second graft conduit attached in fluid communication with the first graft conduit, the method comprising: providing a delivery catheter containing the prosthetic graft in a first delivery configuration; introducing the delivery catheter into a femoral artery on the same side as the common iliac artery bifurcation; advancing the delivery catheter to the common iliac artery bifurcation; and manipulating the delivery catheter to deploy the prosthetic graft in a second expanded configuration such that the first end of the first graft conduit is secured within the lumen of the common iliac artery, the second end of the first graft conduit is secured within the lumen of the external iliac artery and the second graft conduit is secured within the lumen of the internal iliac artery. The delivery catheter may include an angular control element for adjustably controlling the angle between the first and second graft conduits and the method may further include manipulating the angular control element to select a desired angle between the first and second graft conduits. The first graft conduit may include a first stent and the second graft conduit may include a second stent, the first and second stents adapted to expand from a first delivery configuration to a second deployed configuration. The method may further include securing the first end of the first graft conduit within the lumen of the common iliac artery by expanding at least a portion of the first stent to its deployed configuration; the second end of the first graft conduit may be secured within the lumen of the external iliac artery by expanding at least a portion of the first stent to its deployed configuration; and the second graft conduit may be secured within the lumen of the internal iliac artery by expanding the second stent to its deployed configuration.

In a sixth aspect, this invention is a method for repairing an abdominal aneurysm in an aorta which branches into two iliac arteries using a graft system having a first leg which includes first and second ends and a first bifurcated prosthetic graft having a first tubular graft component with first and second ends and a second tubular graft component in fluid communication with the first tubular graft component. The method comprises: providing a delivery system including a first guide wire; advancing the first guide wire through a first iliac artery to a desired location in the aorta above the aneurysm; delivering the first leg over the first guide wire so that the first end of the first leg is above the aneurysm on one side thereof and the second and is on the other side of the aneurysm, the first leg extending across the aneurysm; delivering the first bifurcated prosthetic graft over the first guide wire so that the second tubular graft component is positioned in the internal iliac artery, the first end of the first tubular graft component is positioned in the common iliac artery and the second end of the first graft component is positioned in the external iliac artery; and securing the second end of the first leg to the first end of the first tubular graft component. The first leg may include an aortic stent attached to the first end of the first leg and an iliac stent attached to the second end of the first leg. The first prosthetic graft may include at least one stent attached to the first tubular graft component and a stent attached to the second tubular graft component. The method may further comprise securing the first end of the first leg in the aorta by deploying the aortic stent, securing the second end by deploying the iliac stent and securing the first and second ends of the first tubular graft component by deploying the at least one stent and securing the second tubular graft component by securing the stent attached thereto. Preferably, the first leg is delivered over the first guide wire prior to delivery of the first bifurcated prosthetic graft and the first bifurcated prosthetic graft is delivered over the first guide wire prior to delivery of the first leg. This method may also include providing a first delivery catheter for delivering the first leg and providing a second delivery catheter for delivering the first bifurcated prosthetic graft. The graft system of this method may include a second leg which includes first and second ends and a second bifurcated prosthetic graft having a first tubular graft component with first and second ends and a second tubular graft component in fluid communication with the first tubular graft component; the method then further includes: providing a delivery system including a second guide wire; advancing the second guide wire through the second iliac artery to a desired location in the aorta above the aneurysm; delivering the second leg over the second guide wire so that the first end of the second leg is above the aneurysm and on one side thereof and the second end of the second leg is on the other side of the aneurysm, the second leg extending across the aneurysm; delivering the second bifurcated prosthetic graft over the second guide wire so that the second tubular graft component is positioned in the second internal iliac artery, the first end of the first tubular graft component is positioned in the second common iliac artery and the second graft component is positioned in the second external iliac artery; and securing the second end of the second leg to the first end of the first tubular graft component of the second prosthetic graft.

In a seventh aspect, this invention is a method for repairing an abdominal aneurysm using a graft system having a first leg which includes first and second ends and a first bifurcated prosthetic graft having a first tubular graft component with first and second ends and a second tubular graft component in fluid communication with the first tubular graft component, comprising: advancing the first leg through a first iliac artery into the aorta so that the first end of the first leg is above the aneurysm on one side thereof and the second end is on the other side of the aneurysm, the first leg extending across the aneurysm; after the first leg has been advanced, advancing the first bifurcated prosthetic graft through the same iliac artery so that the second tubular graft component is positioned in the internal iliac artery, the first end of the first tubular graft component is positioned in the common iliac artery and the second end of the first graft component is positioned in the external iliac artery; and securing the second end of the first leg to the first end of the first tubular graft component. The graft system may include a second leg having first and second ends and a second bifurcated prosthetic graft having a first tubular graft component with first and second ends and a second tubular graft component in fluid communication with the first tubular graft component. The method then further comprises: advancing the second leg through the second iliac artery into the aorta so that the first end of the second leg is above the aneurysm on one side thereof and the second end of the second leg is on the other side of the aneurysm, the second leg extending across the aneurysm; and after the second leg has been advanced, advancing the second bifurcated prosthetic graft through the same iliac artery as the second leg so that the second tubular graft component of the second bifurcated prosthetic graft is positioned in the second internal iliac artery, the first end of the first tubular graft component is positioned in the second common iliac artery and the second end of the first graft component is positioned in the second external iliac artery; and securing the second end of the second leg to the first end of the first tubular graft component of the second bifurcated prosthetic graft.

In an eighth aspect, this invention is a graft system for repairing an abdominal aneurysm comprising a first leg having first and second ends, the first end adapted to be secured in the aorta on one side of the aneurysm and the second end adapted to be secured on the other side of the aneurysm; a first bifurcated prosthetic graft having a first tubular graft component with first and second ends and a second tubular graft component attached in fluid communication with the first tubular graft component, the first end of the first tubular graft component adapted to be secured in the common iliac artery, the second end of the first tubular graft component adapted to be secured in the external iliac artery and the second tubular graft component adapted to be secured in the internal iliac artery; a first guide wire sized to fit through a first iliac artery and through the aorta to a location above the aneurysm; a first delivery catheter configured to advance and deliver the first leg across the first guide wire; and a second delivery catheter configured to advance and deliver the first prosthetic graft across the first guide wire. The graft system may include first leg having an aortic stent attached to the first end and an iliac stent attached to the second end. The first bifurcated prosthetic graft may have at least one stent attached to the first tubular graft component and a stent attached to the second tubular graft component. Preferably, the graft system includes: second leg having first and second ends, the first end adapted to be secured in the aorta on one side of the aneurysm and the second end adapted to be secured on the other side of the aneurysm; a second bifurcated prosthetic graft having a first tubular graft component with first and second ends and a second tubular graft component attached in fluid communication with the first tubular graft component, the first end of the first tubular graft component adapted to be secured in the common iliac artery, the second end of the first tubular graft component adapted to be secured in the external iliac artery and the second tubular graft component adapted to be secured in the internal iliac artery; a second guide wire sized to fit through the second iliac artery and through the aorta to a location above the aneurysm; a third delivery catheter configured to advance and deliver the second leg across the second guide wire; and a fourth delivery catheter configured to advance and deliver the second prosthetic graft across the second guide wire.

DETAILED DESCRIPTION OF THE PREFERRED EMBODIMENTS

The present invention is a prosthetic graft for use with a graft system used to repair the treatment of aortic aneurysms which extend into at least one common iliac artery and do not have a suitable region for seating a stent or other attachment device. The graft is designed to be used in combination with a graft system having legs extending into the common iliac arteries and provides the graft system with a place to securely seat its iliac legs without blocking the internal iliac artery.

The terms "distal" and "proximal" as used herein refer only to the delivery catheter of the prosthetic graft, not to the vasculature. The present method contemplates advancement of the delivery catheter in a retrograde manner (i.e., against the flow of blood). Therefore, "proximal" refers to a location closer to the physician and "distal" refers to a location farther from the physician. The vasculature is referred to with respect to the cranial (closer to head) and caudal (closer to feet) directions. Also, as used in this specification, the term "above", in the context of relative positioning, with respect to the aneurysm, refers to the regional cranial of the aneurysm, for example, within the aorta, whereas "below" refers to the region of the vasculature caudal of the aneurysm, for example, within the common iliac arteries.

Figure 14:
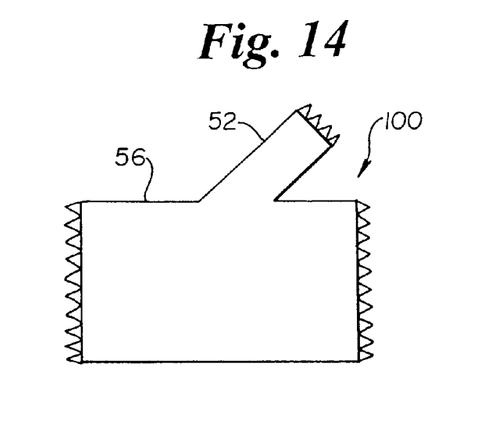
FIG. 14 is a plan view of the deployed prosthesis.
Figure 15:
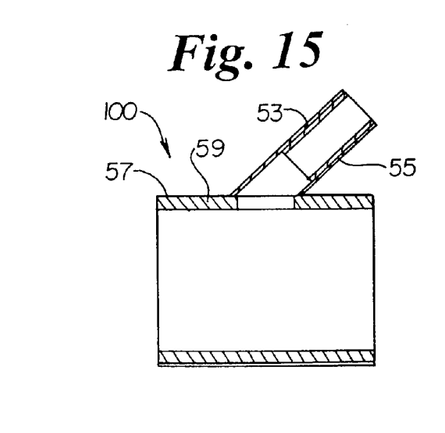
FIG. 15 is a cross-sectional view of the deployed prosthesis.

As best seen in FIGS. 14 and 15, the prosthesis includes a common/external iliac leg 56 and an internal iliac leg 52. Each leg 56 and 52 includes a graft component 57 and 53, and a stent component 59 and 55, respectively. Both legs are generally tubular having a circular cross-section. The common/external iliac leg has an upper portion which is positioned above the junction of the common iliac artery with the internal iliac artery and the lower portion which is positioned in the external iliac artery below the internal iliac artery. The internal iliac leg is attached to and projects from the common/external iliac leg and is positioned within the internal iliac artery. The attachment between the graft and stent is preferably by sutures. The prosthesis is delivered by way of a delivery catheter in a first contracted position. Once properly located the stent components expand radially during deployment so that the legs of the prosthetic graft are secured at the iliac bifurcation in their proper position.

The prosthesis is advanced into the iliac artery by means of a catheter. Typically, a guide catheter is introduced into the patient's vasculature via the femoral artery, through an incision made at a location where the vessel is close to the undersurface of the skin. A guide wire is snaked through the vasculature to a point above the aneurysm. The guide wire may be made of stainless steel or the like and is conventionally covered with an inert material (e.g., polytetrafluoroethylene (PTFE)). The guide wire may remain in a fixed position throughout the endoluminal bypass procedure. The catheter of this invention is then guided into the aneurysm along this guide wire and the prosthesis is deployed in the iliac artery.

Figure 1:
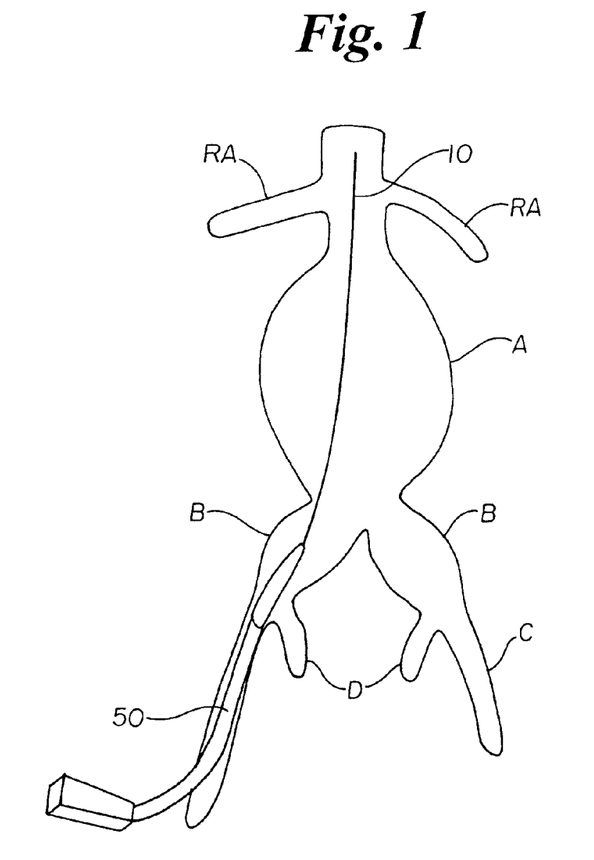
FIG. 1 is a diagrammatic view of a portion of a human vascular system depicting an abdominal aortic aneurysm extending from below the renal arteries and into the common iliac arteries and showing advancement along a guide wire of a delivery catheter containing the prosthetic graft of the present invention.

FIG. 1 shows an aneurysm A in the infrarenal aorta and extending into the common iliac arteries. The infranrenal aorta is that portion of the aorta disposed between the left and right renal arteries RA and the common iliac arteries B which branch left and right. Each common iliac artery branches into internal and external iliac arteries D and C, respectively. External iliac artery C becomes the femoral artery below the inguinal ligament. Internal iliac artery D is also called the hypogastric artery. Delivery catheter 50 is shown advancing along guide wire 10 to the common iliac bifurcation site of the external and internal iliac arteries C and D.

Figure 9:
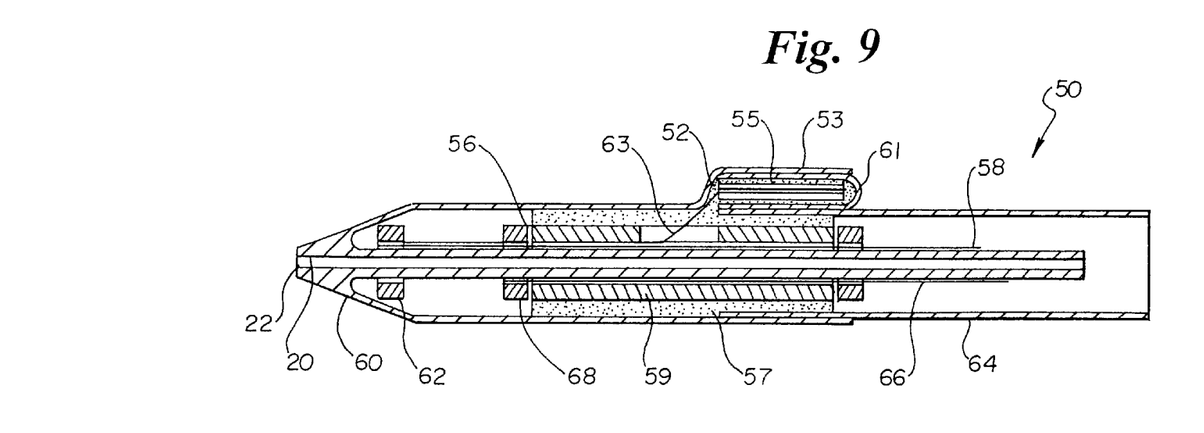
FIG. 9 is a view of the delivery catheter assembly and prosthetic graft.

FIG. 9 is a cross-sectional view of the distal portion of delivery catheter assembly 50 used to introduce and deploy the prosthetic graft. Inner shaft 20 runs the length of delivery catheter assembly 50. Inner shaft 20 defines a central bore, or guide wire lumen, 22, which provides a means for inserting the catheter assembly into a patient along the guide wire (shown as 10 in FIGS. 1 to 7). Inner shaft 20 is fabricated from a suitable polymer, such as HDPE, though other polymers as well as metallic materials may be used. Lumen 22 allows catheter assembly 50 to pass coaxially over a guide wire (such as a 0.035 inch diameter stainless steel guide wire typically used for endovascular procedures in the aorta and iliac arteries).

About inner shaft 20 is mounted main body sheath 64 in slidable engagement with nose cone 60. Main body sheath 64 is fabricated from a biocompatible polymer such as PTFE or from polymer/metal composites. Composite materials may be particularly useful in adding strength and kink resistance to the main body sheath. The prosthetic graft 100 is contained in the compartment formed between inner shaft 20, and the combination of main body sheath 64 and nose cone 60. This compartment also provides a conduit from the proximal to the distal portion of the delivery catheter for passage of cold saline and radiographic contrast solution.

Nose cone 60 is fabricated from a flexible polymeric material or from metallic materials. Nose cone 60 provides a stiffness transition between the relatively flexible guide wire and the stiffer main sheath body 64. The distal tip of the delivery catheter is designed to be more flexible at its distal-most portion and increasingly stiffer proximally. This arrangement will provide a strain-relieving effect, which aids in the tractability of the device in tortuous artery bends.

As noted previously, prosthetic graft 100 includes internal iliac leg 52 and common/external iliac leg 56. Internal iliac leg 52 preferably includes a graft material component 53 and a stent material component 55. Common/external iliac leg 56 preferably includes a graft material component 57 and a stent material component 59. The graft material component of each leg is connected to the stent material component, preferably by sutures.

The graft material components may be made of materials which include woven and knitted materials comprising polyester, polytetrafluoroethylene (PTFE), silicones, and urethanes. The materials may be porous or non-porous and may be opaque to X-rays. Preferred materials include polyester fabric, for example, DACRON®, TEFLON®, or other suitable fabric. A preferred fabric for use in the graft component is a 40 denier polyester yarn, having 180 to 250 end yarns per inch and 80 to 120 pick yarns per inch. At this weave density, the graft component is relatively impermeable to blood flow through the wall, but is relatively thin, ranging between 0.08 and 0.12 mm wall thickness. Preferably, the graft components are woven as tubes.

The stent material components are preferably self-expandable and are comprised of a shape memory alloy. Such an alloy can be deformed from an original, heat-stable configuration to a second, heat-unstable configuration. When in the second heat-unstable configuration the application of a desired temperature causes the alloy to revert to an original heat-stable configuration. A particularly preferred shape memory alloy is binary nickel titanium comprising 55.8% Ni by weight. This NiTi alloy undergoes a phase transformation at physiological temperatures. A stent made of this material is deformable when chilled. Thus, at low temperatures, (e.g., below 20° C.), the stent is compressed so it can be delivered to the desired location. The stent is kept at low temperatures by circulating chilled saline solution. The stent expands when the chilled saline is removed and it is exposed to higher temperatures, (e.g., 37° C.).

Preferably, the stent is fabricated from a single piece of alloy tubing. The tubing is laser cut, shape-set by placing the tubing on a mandrel, heat-set to its desired expanded shape and size and electropolished. Electropolishing smoothes the surface of the alloy, which is believed to improve fatigue properties as well as extend the strain-to-fracture and also improves thrombogenicity resistance. Preferably, the shape setting is performed at 550° C. for approximately 20 minutes, followed by aging at 470° C. for 10 minutes. This heat treatment process provides for a stent that has a martensite to austenite transformation temperature range of less than 15 Celsius degrees and an austenite finish temperature ($A_f$) of slightly less than 37° C.

Figure 10:
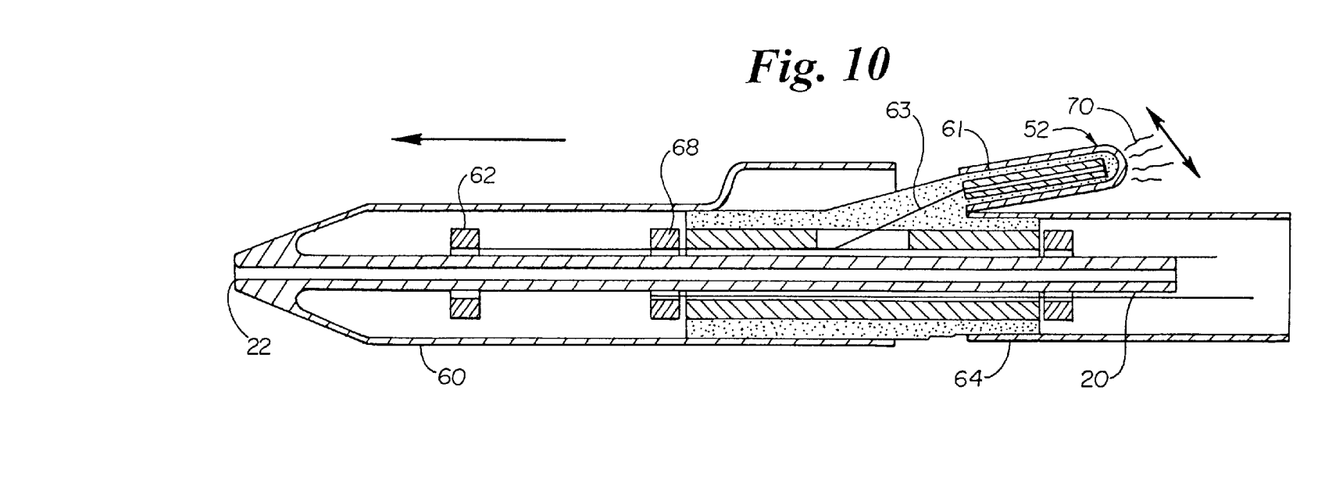
FIG. 10 is a view of the delivery catheter assembly illustrating the lateral projection of the undeployed internal iliac leg and injection of radiographic contrast solution.

The proximal portion of main body sheath 64 is connected to a manifold (not shown) which is connected to reservoirs holding radiographic contrast solution and chilled saline. As best seen in FIG. 10, chilled saline and/or radiographic contrast solution 70 flow through main body sheath 64 and out through orifices located at the tip of nose cone 60 and at the tip of internal iliac leg prosthesis 52.

Also within main body sheath 64 are sheath control rod 58 and stent retainer rod 66. The sheath control rod 58 extends from the proximal end to the distal portion of the catheter. The distal portion of the sheath control rod 58 is rigidly attached to sheath control rod slip ring 62. Sheath control rod slip ring 62 has a sliding fit with inner shaft 20. Sheath control rod slip ring 62 is also rigidly affixed to a shorter proximally facing iliac leg sheath control rod 63. Iliac control rod 63 is positioned coaxially within the internal iliac leg 52 of the prosthesis. Sheath control rod 63 is pre-formed to preferentially extend laterally from the axis of the main catheter when unrestrained by nose cone 60. In the completely unrestrained position sheath control rod 63 causes internal iliac leg 56 to assume an angle of between about 45° and 90° with the longitudinal axis of the delivery catheter. Sheath control rod 63 is rigidly attached to internal iliac sheath 61. The retraction of sheath control rod 58 (in a proximal direction) slides internal iliac sheath 61 relative to internal iliac leg 52, thus exposing the internal iliac leg 52. When exposed to body temperature, the stent component of the internal iliac leg 52 expands.

Stent retainer rod 66 is connected to stent retaining slip rings 68 located at the proximal and distal ends of common/external iliac leg 56. Slip rings 68 surround the external/common iliac leg and prevent axial movement of the leg during advancement of the nose cone and inner lumen 20 during the retraction of sheath control rod 58 and/or the retraction of main body sheath 64. Stent retainer rod 66 is preferably made of stainless steel. Preferably, slip rings 68 are made of platinum so they can provide radiopaque markings for angiographic visualization of the prosthesis location. Slip rings 68 maintain a sliding fit with inner shaft 20, which allows relative movement between stent retainer rod 66 and inner shaft 20. The proximal portion of stent retainer rod 66 is attached to a manifold (not shown) that provides the relative anchoring and positioning of the assembly, main body sheath 64, and inner shaft 20.

Chilled saline flows through main body sheath 64, keeping the stent components of both legs cold. Expansion of the stent components 55 and 59 of internal iliac leg 52 and external/common iliac leg 54 by exposing them to body temperature results in fully deploying prosthesis 100.

Figure 3:
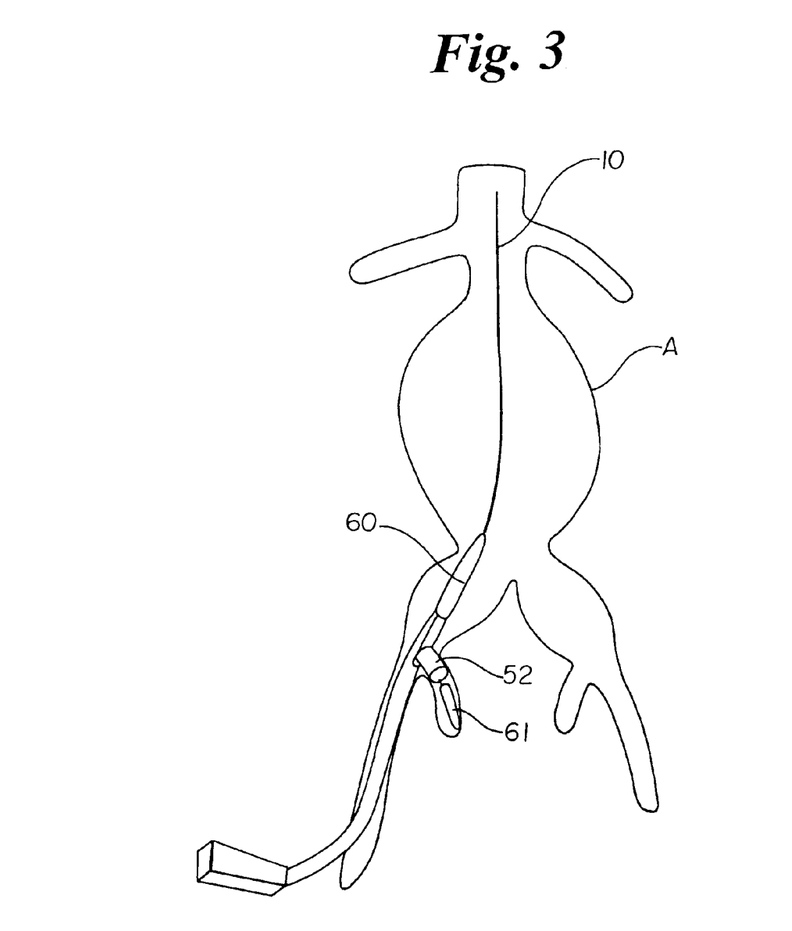
FIG. 3 is a view of the aneurysm of FIG. 1 showing deployment of the internal iliac leg of the prosthetic graft.

Internal iliac leg sheath 61 is made from a polymer such as high density polyethylene (HDPE), though other polymers as well as metallic materials may be used. Sheath 61 surrounds internal iliac leg 52 and serves to navigate leg 52 into the internal iliac artery. Sheath 61 preferably has a tapered segment at the distal end that provides an atraumatic surface for navigation into internal iliac artery B. The tip of sheath 61 may also have one or more orifices for the delivery of radiographic contrast solution (such as depicted in FIGS. 3 and 10) and/or chilled saline. Although not shown, the delivery catheter may be provided with separate lumens for the delivery of contrast solution and chilled saline.

Figure 2:
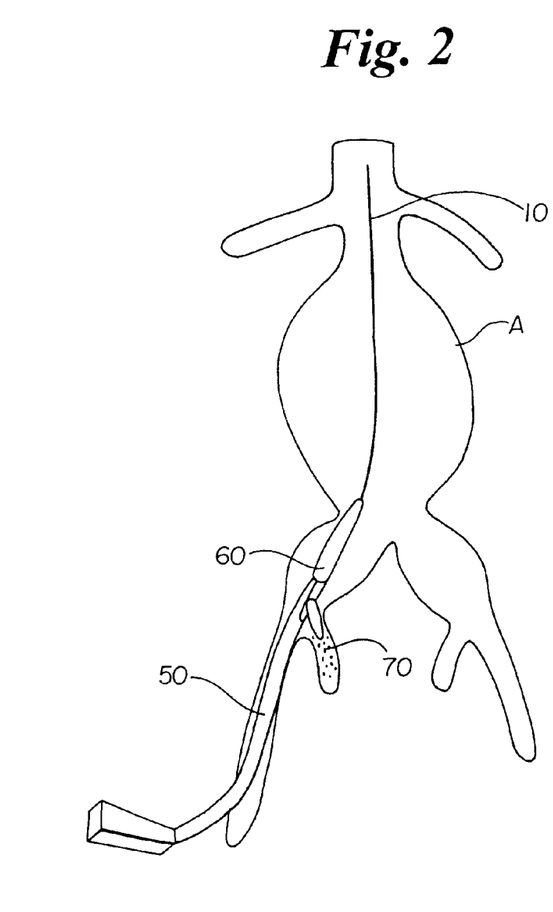
FIG. 2 is a view of the aneurysm of FIG. 1 showing injection of radiographic contrast solution at the internal iliac artery and projection of the undeployed internal iliac leg of the prosthetic graft into the internal iliac artery.

FIGS. 9 to 13 show the steps of deploying prosthesis 100 while FIGS. 1–8 show how those steps relate to the introduction, positioning, and deployment of the prosthetic graft to repair an abdominal aortic aneurysm in the vasculature of a human. FIG. 9 is a cross-section of the delivery catheter assembly and prosthetic graft 100 in the fully undeployed configuration which it would be in while the delivery catheter is advanced to the branch of the common and internal iliac arteries as seen in FIG. 1. In FIG. 10, inner shaft 20 and nose cone 60 have been advanced allowing the internal iliac leg 52 to deflect laterally. Radiographic contrast solution 70 is flowing from an orifice at the tip of internal iliac leg 52. The angle of deflection can be controlled by the relative position of nose cone 60 with regards to the sheath control rod 63. The more the nose cone 60 is advanced, the greater the lateral angulation will be. The preform in the sheath control rod 63 will determine the maximum unrestrained angle of the extended internal iliac leg 52 and sheath 61. Catheter assembly 50 can be translated and rotated to position internal iliac leg 52 into the internal iliac artery as seen in FIG. 2.

Figure 11:
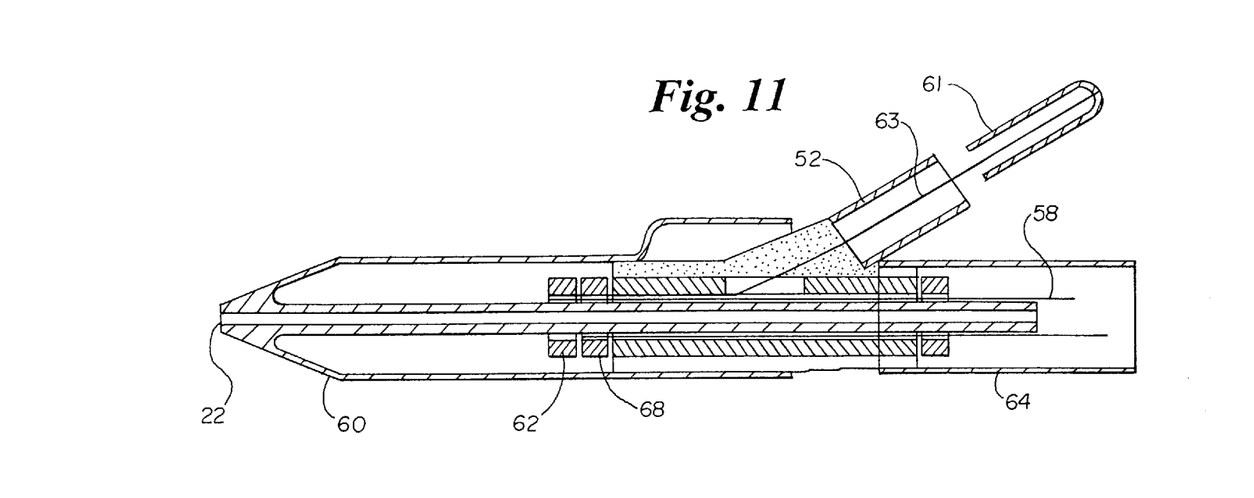
FIG. 11 is a view of the delivery catheter assembly illustrating deployment of the internal iliac leg of the prosthesis.

In FIG. 11, sheath control rod 58 has been retracted in a proximal direction. This movement advances internal iliac leg sheath 61 off the distal end of internal iliac leg 52. The body temperature causes the stent component 55 of internal iliac leg 52 to expand into the iliac artery as seen in FIG. 3.

Figure 4:
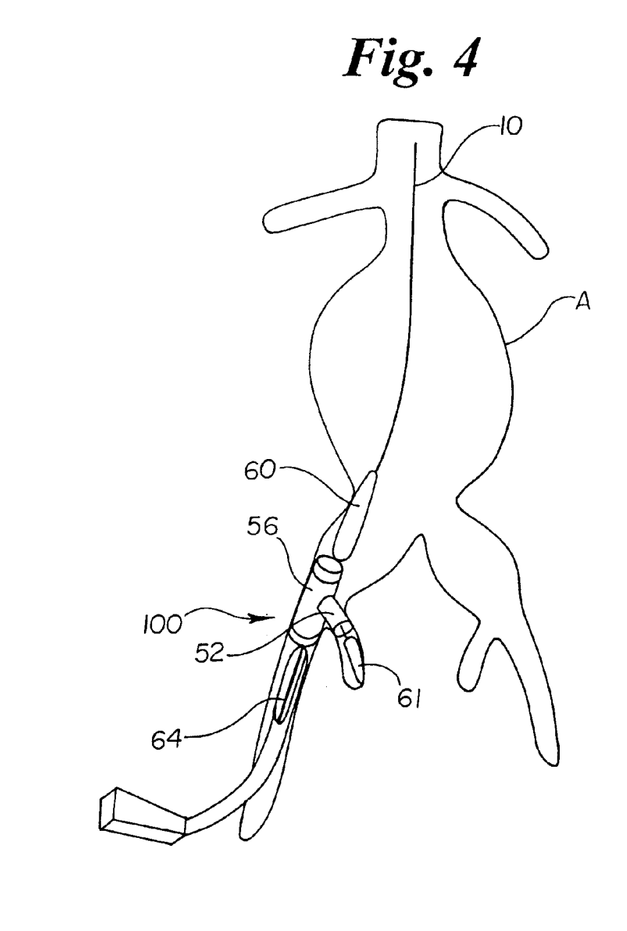
FIG. 4 is a view of the aneurysm of FIG. 1 showing deployment of the common/external iliac leg of the prosthetic graft.
Figure 5:
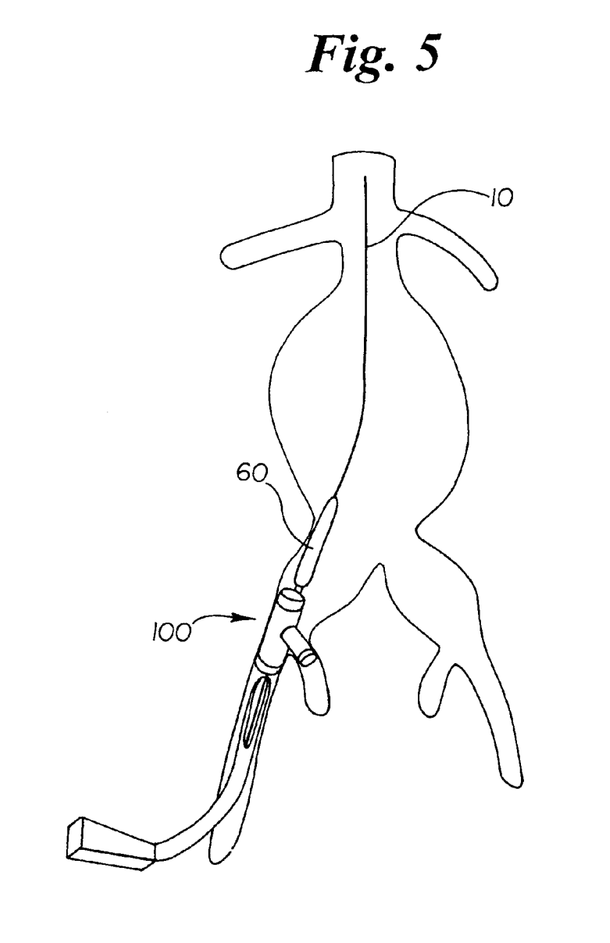
FIG. 5 is a view of the aneurysm of FIG. 1 showing advancement of the control rod and advancement of the internal iliac sheath into the nose cone.
Figure 12:
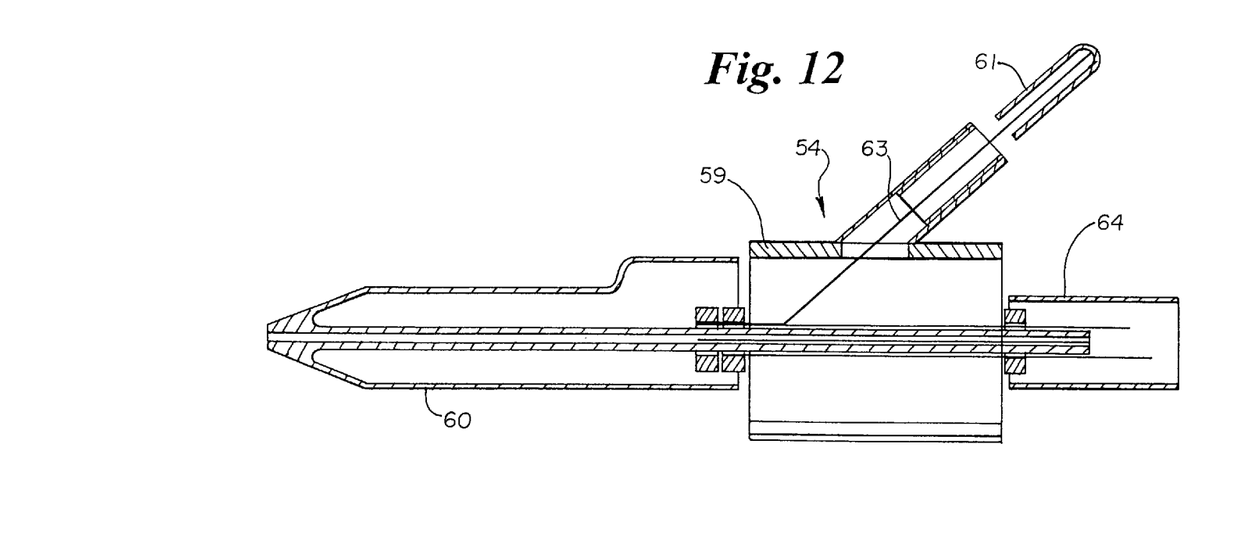
FIG. 12 is a view of the delivery catheter assembly illustrating expansion of the common/external iliac leg of the prosthesis.

In FIG. 12, main body sheath 64 has been retracted and nose cone 60 further advanced, thus exposing the stent component 59 of common/external iliac leg 54 to body temperature. The leg 54 then expands into the common iliac artery. The position of the prosthetic graft 100 is shown in FIG. 4.

Figure 6:
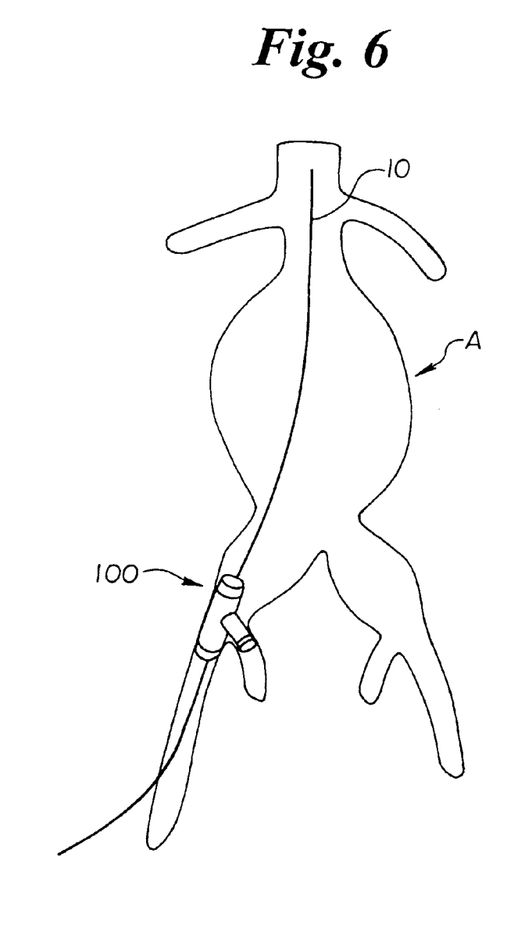
FIG. 6 is a view of the aneurysm of FIG. 1 after the delivery system has been removed.
Figure 13:
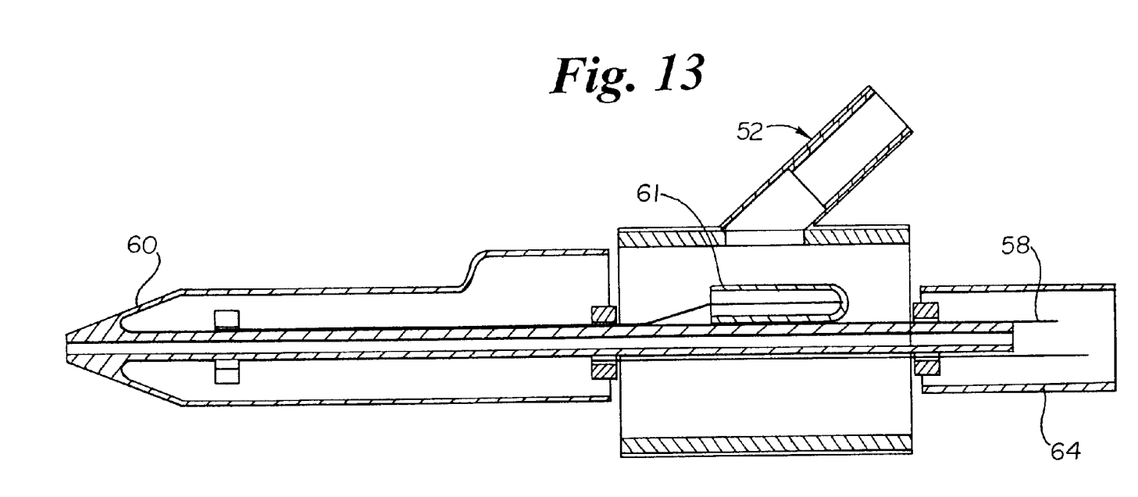
FIG. 13 is a view of the delivery catheter assembly showing movement of the internal iliac sheath into the nose cone.

In FIG. 13, sheath control rod 58 has been advanced distally until the internal iliac leg sheath 61 is completely inside the common/external iliac leg. This is the position shown in FIG. 5. Once sheath 61 is contained in the common/external iliac leg, the entire catheter assembly can be withdrawn leaving only prosthesis 100 as seen in FIG. 6. Although a particular sequence of deploying the internal iliac leg and the upper (common iliac) and lower (external iliac) portions of the common/external iliac has been shown it will be appreciated that the delivery system allows deployment in any desired sequence.

Figure 7:
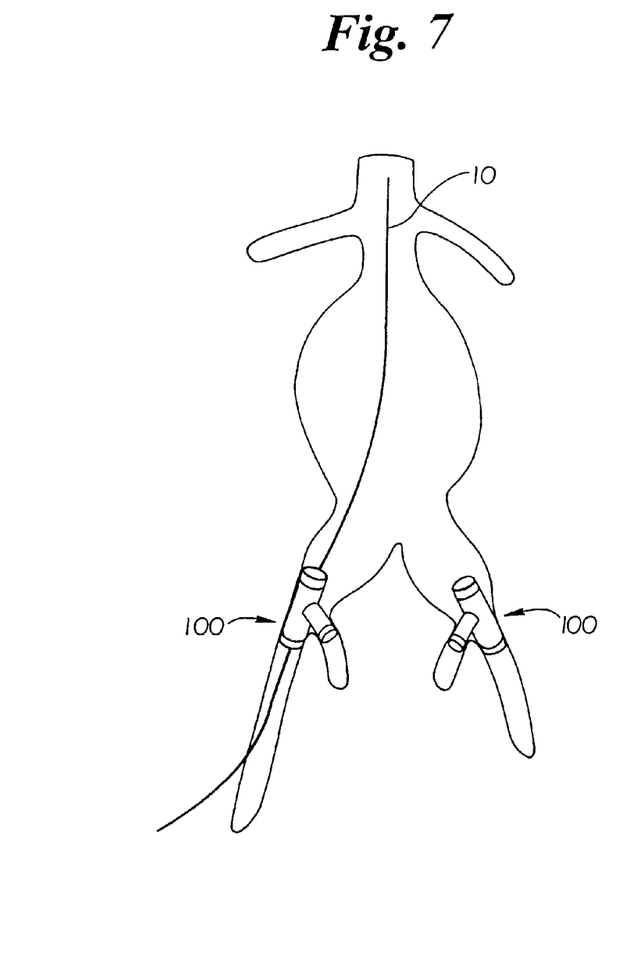
FIG. 7 is a view of the aneurysm of FIG. 1 illustrating deployment of a prosthetic graft in both iliac arteries.

FIGS. 14 and 15 are plan and cross-sectional views of the fully deployed prosthesis 100. The prosthesis is sized to fit within and sealingly engage the walls of the vessel at the common iliac bifurcation. Preferably, the diameter of the legs of the prosthetic graft are oversized so they are about 2 to 4 mm larger than the diameter of the vessel itself. The longitudinal length of the external/common iliac leg is within the range of about 4 to 12 cm. The longitudinal length of the internal iliac leg is in the range of about 1 to 4 cm. The diameter of the fully deployed external/common iliac leg is about 6 to 18 mm while the diameter of the fully deployed internal iliac leg is about 4 to 8 mm. FIG. 7 shows the prosthetic graft of the present invention deployed in both of the common iliac arteries. The procedure for introducing, positioning, and deploying the second graft are the same as those discussed above except that entry is through the femoral artery on the other side of the patient.

Figure 8:
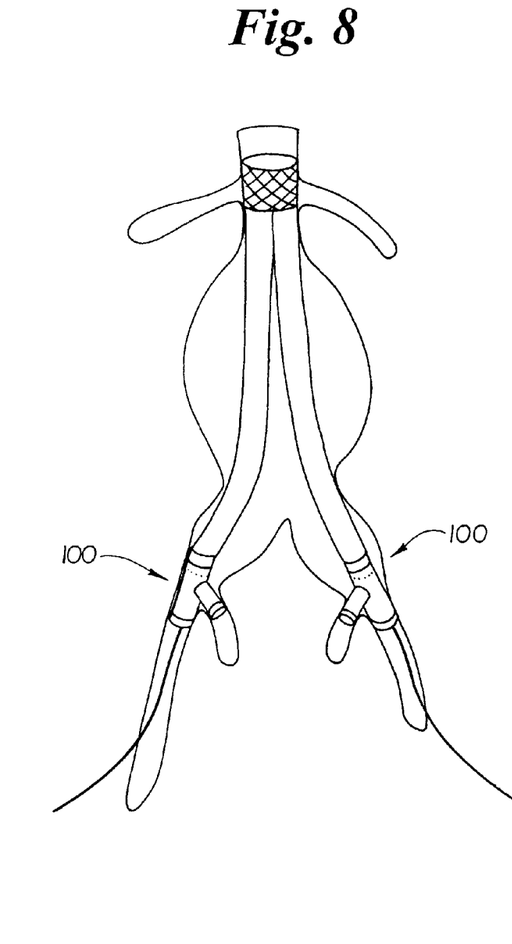
FIG. 8 is a view similar to the aneurysm of FIG. 7 showing the prosthetic grafts combined with a biluminal endovascular graft system to repair the aneurysm.

FIG. 8 shows the prosthetic grafts 100 of FIG. 7 connected to the lower or iliac portion of the legs of a biluminal endovascular graft system used to repair the aortic aneurysm. The prosthetic grafts of the present invention could be used in connection with any biluminal graft system which includes separate legs or conduits for each iliac artery. Such a system is disclosed in co-pending patent application entitled "Biluminal Endovascular Graft System", filed Mar. 16, 1998 as Ser. No. 09/039776, the disclosure of which is incorporated herein by reference. An advantage of the present invention is that the prosthetic graft of the present invention can be delivered over the same guide wire as the individual legs of the biluminal aortic graft system. A single guide wire introduced through the right femoral artery can be used for delivery of one leg of the biluminal aortic stent and one bifurcated prosthetic graft or a second guide wire introduced through the left femoral artery is used for delivery of the second leg of the biluminal aortic graft and the second prosthetic graft.

The biluminal aortic graft system could be deployed either before or after the prosthetic graft 100. If prosthetic grafts 100 are deployed first, then the iliac legs of the biluminal aortic graft system are deployed into the upper portion of the common/external iliac legs of the prosthetic graft, with a minimum of a 2 cm overlap. This ensures proper attachment and seating of the legs of the aortic graft without blocking the internal iliac arteries. If the biluminal aortic graft is deployed before prosthetic grafts 100 then prosthetic grafts 100 would be deployed into the iliac legs of the aortic graft, with a minimum of a 2 cm overlap. In either case, the graft sizes will be selected to ensure proper attachment and seating of the grafts. The means of attachment of the grafts may include barbs or hooks on the stents of one or both systems (not shown) to ensure a secure attachment.

Figure 19:
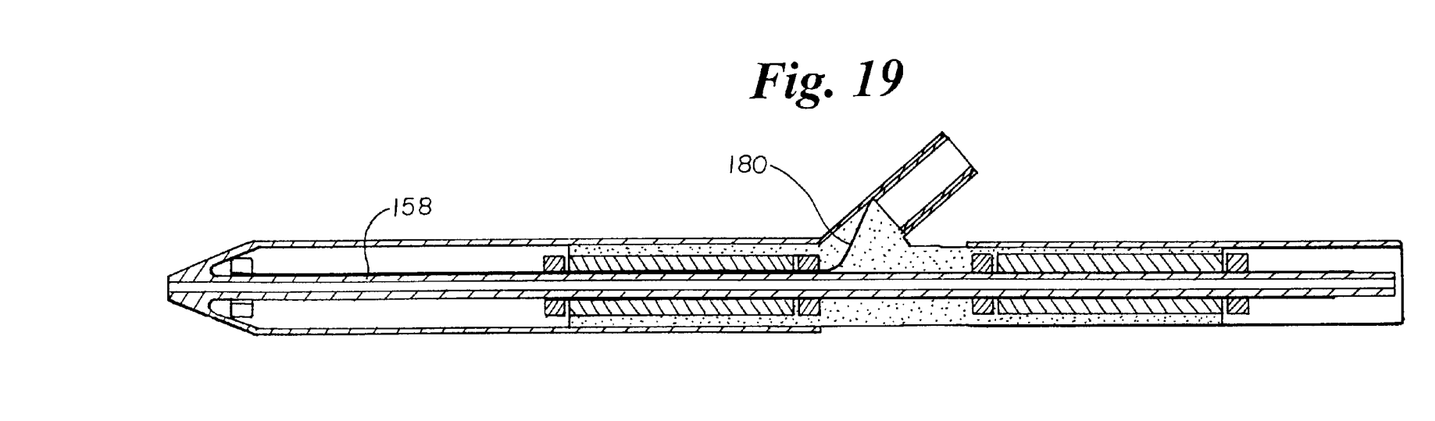
Figure 20:
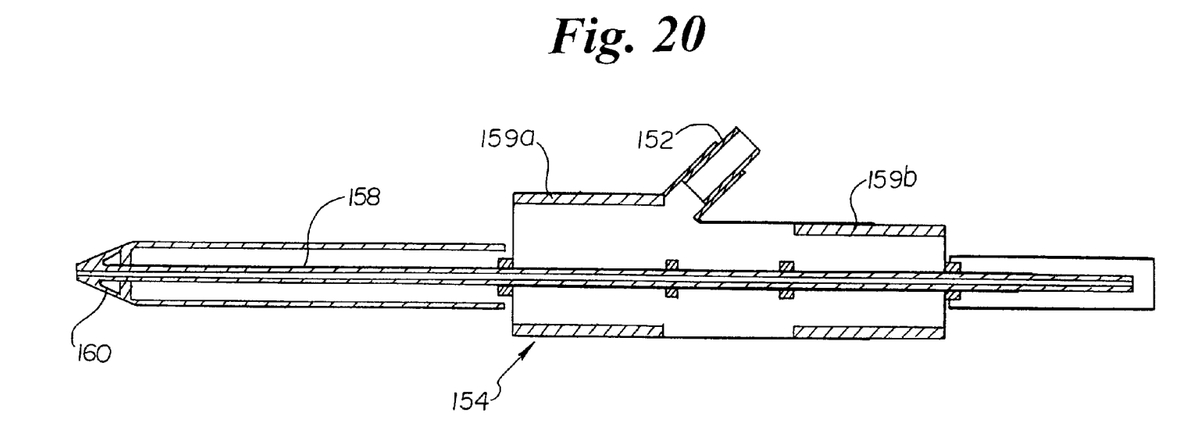
Figure 21:
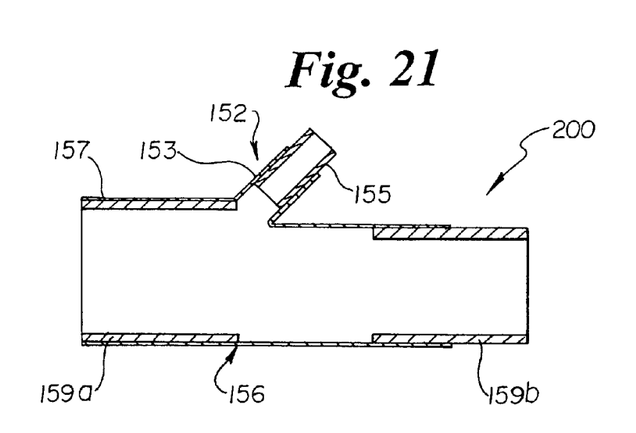
FIG. 21 is a cross-sectional view of the second embodiment of the prosthetic graft of the present invention.

FIG. 21 is a cross-sectional view of a second embodiment of a prosthetic graft 200 in accordance with the present invention. FIGS. 16–20 are cross-sectional views of the prosthetic graft 200 loaded into a delivery catheter 150 during various stages of the deployment process.

As seen in FIG. 21, the prosthesis includes a common/external iliac leg 156 and an internal iliac leg 152. Leg 156 includes common/external artery graft component 157 and a common iliac artery stent component 159a and an external iliac artery stent component 159b. Leg 152 includes a graft component 153 and a stent component 155. The materials which make-up the graft and stent components of prosthetic graft 200 are similar to those described with respect to those used in prosthetic graft 100.

By fabricating the common/external iliac leg 156 from separate stent components which are spaced apart from one another, the internal iliac leg 152 is allowed to be positioned closer to the longitudinal center line of the delivery catheter when collapsed. This configuration results in a reduction in the diameter of the delivery system. The use of separate stents for the common iliac and external iliac arteries also allows flexibility in sizing at each end of the prosthetic graft. Preferably, the longitudinal length of the common/external iliac leg 156 is about 8 to 12 cm. The longitudinal length of the internal iliac leg 152 is about 1 to 4 cm. The diameter of the common iliac portion of the common/external iliac leg 156 is about 12 to 18 mm. The diameter of the external iliac portion of the common/external iliac leg 156 is about 6 to 12 mm.

Figure 16:
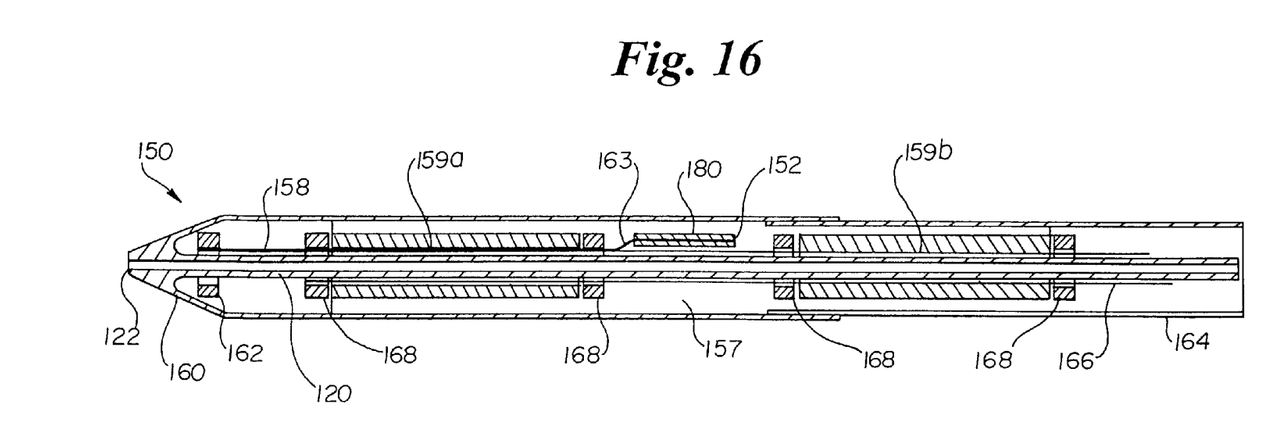
FIGS. 16–20 are cross-sectional views of a second embodiment of the prosthetic graft loaded into a delivery catheter during various stages of the deployment process.

FIG. 16 is a cross-sectional view of the distal portion of delivery catheter assembly 150 used to introduce and deploy prosthetic graft 200. Inner shaft 120 runs the length of delivery catheter assembly 150. Inner shaft 120 defines a central bore, or guide wire lumen 122 which provides a means for inserting the catheter assembly into a patient along the guide wire. Guide wire lumen 122 allows catheter assembly 50 to pass coaxially over a guide wire.

About inner shaft 120 is mounted main body sheath 164 in slidable engagement with nose cone 160. Prosthetic graft 200 is contained in the compartment formed between inner shaft 120, and the combination of main body sheath 164 and nose cone 160. This compartment also provides a conduit from the proximal to the distal portion of the delivery catheter for passage of cold saline and radiographic contrast solution.

As in the previous embodiment, nose cone 160 provides a stiffness transition between the relatively flexible guide wire and the stiffer main body sheath 164.

The proximal portion of main body sheath 164 is connected to a manifold (not shown) which is connected to reservoirs holding radiographic contrast solution and chilled saline. As in the previous embodiment, chilled saline and/or radiographic contrast solution 70 flows through main body sheath 164 and out through orifices located at the tip of nose cone 160 and at the tip of internal iliac leg prosthesis 152.

Also located within main body sheath 164 are sheath control rod 158 and stent retainer rod 166. The sheath control rod 158 extends from the proximal end to the distal portion of the catheter. The distal portion of the sheath control rod 158 is rigidly attached to sheath control rod slip ring 162. Sheath control rod slip ring 162 has a sliding fit with inner shaft 120. Sheath control rod slip ring is also rigidly affixed to a shorter proximally facing iliac leg control rod 163. Iliac control rod 163 is positioned coaxially within the internal iliac leg 152 of the prosthesis. Iliac control rod 163 is pre-formed to preferentially extend laterally from the axis of the main catheter when unrestrained by nose cone 160. In the completely unrestrained positioned, iliac control rod 163 causes internal iliac leg 156 to assume an angle of between about 45° to 90° with the longitudinal axis of the delivery catheter. A filament sheath 180 is wrapped around internal iliac leg 152. The filament sheath may be fabricated of PTFE suture, however, other metallic and/or polymeric materials may be used. The filament is anchored to prosthetic graft 200 at a point 182 (FIG. 18) and is wrapped around the stent component of the internal iliac leg and attached to iliac control rod 163 at the proximal portion of the leg. The retraction of sheath control rod 158 (in a proximal direction) slides iliac control rod 163 out the end of iliac leg 152 causing the end of iliac control rod 163 to disengage with filament sheath 180, thus allowing the filament sheath to unwind. The wound filament sheath provides a sealing conduit for the application of the chilled saline to leg 152. The filament may be a tightly wound thread or an overlapping ribbon or any other configuration which results in the formation of a substantially closed circuit. Once the filament is removed the body's temperature allows the stent to expand.

Stent retainer rod 166 is connected to stent retainer slip rings 168 located at the proximal and distal ends of stent components 159a and 159b. Slip rings 68 prevent axial movement of the leg during advancement of the nose cone and inner lumen 120 during the retraction of sheath control rod 158 and/or the retraction of main body sheath 164. Slip rings 168 maintain a sliding fit with inner shaft 120 which allows relative movement between stent retainer rod 166 and inner shaft 120. The proximal portion of stent retainer rod 166 is attached to a manifold (not shown) that provides the relative anchoring and positioning of the assembly, main body sheath 164, and inner shaft 120.

The introduction, positioning, and deployment of prosthetic graft 200 is similar to that described with respect to prosthetic graft 100. FIG. 16 is a cross-section of the delivery catheter system and prosthetic graft 200 in the fully undeployed configuration it would have while the catheter is advanced to the branch of the common and internal iliac arteries. The position would be similar to that seen in FIG. 1.

Figure 17:
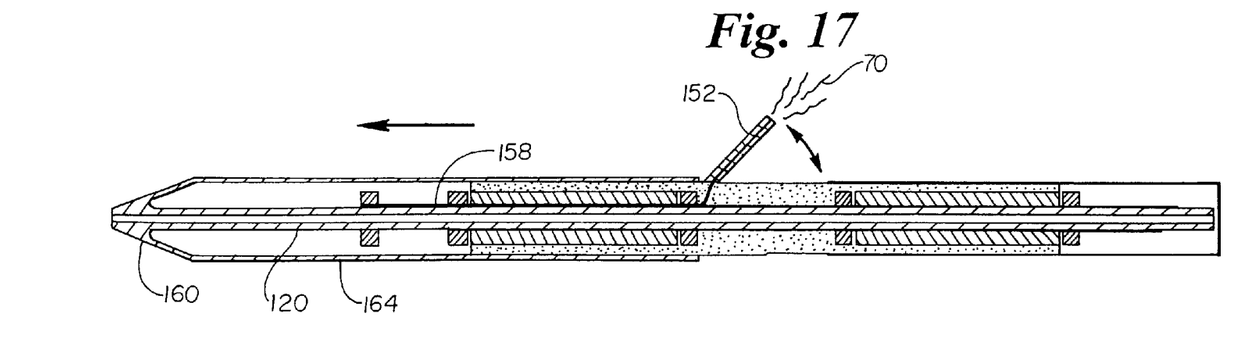
Figure 18:
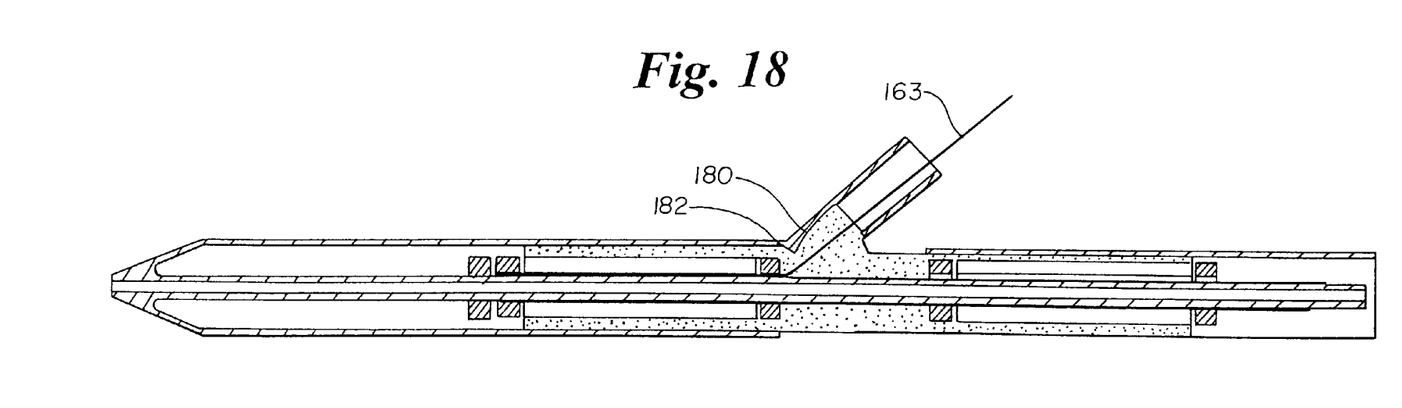

In FIG. 17, inner shaft 120 and nose cone 160 have been advanced allowing the internal iliac leg 152 to deflect laterally. Radiographic contrast solution 70 is flowing through internal iliac leg 152 and nose cone 160. The angle of deflection can be controlled by the relative position of nose cone 160 with regards to iliac control rod 163. The more nose cone 160 is advanced, the greater the lateral angulation will be. The pre-form in the internal iliac control rod 163 will determine the maximum unrestrained angle of the extended internal iliac leg 152. Catheter assembly 150 can be translated and rotated to position the internal iliac leg 152 into the internal iliac artery in a manner similar to that illustrated in FIG. 2. When internal iliac leg 152 has been positioned into the internal iliac artery (FIG. 18), sheath control rod 158 is retracted in the proximal direction as shown in FIG. 19. This movement dislodges iliac leg control rod 163 from filament sheath 180. Exposure of iliac leg stent component 155 to body temperature causes it to expand in the same position shown generally in FIG. 3.

In FIG. 20, the sheath control rod 158 is advanced in the distal direction until the control rod 163 is completely inside nose cone 160. The main body sheath 164 has been retracted and nose cone 160 has been further advanced, thus exposing stent components 159a and 159b of common/external iliac leg 154 to body temperature. Leg 154 then expands into the common iliac artery such that the position of stent 159a lies above the junction with the internal iliac artery and stent 159b lies below the junction with the internal iliac artery. The position of prosthetic graft 200 is similar to that shown in FIG. 4. At this point, delivery catheter 150 is withdrawn through the lumen of common/external iliac leg 156.

The prosthetic graft 200 can be used in the same manner as that described with respect to prosthetic graft 100.

What is claimed is:

1. A method for placing a prosthetic graft in a vessel of a patient's vascular system, the prosthetic graft having a first tubular graft component and a second tubular graft component in fluid communication with the first tubular graft component, the method comprising:

providing a delivery catheter containing the prosthetic graft in a first delivery configuration, the catheter having an angular control element for adjustably controlling the angle between the first and second tubular graft components;

advancing the catheter through the vessel to a desired location;

manipulating the delivery catheter to adjust the angular control element to select a desired angle between the first and second tubular graft components; and deploying the prosthetic graft in the vessel in a second expanded configuration.

2. The method of claim 1 wherein the angular control element of the catheter includes a wire with a preformed angle and wherein the step of manipulating the angular control element to select a desired angle includes advancing or retracting the wire.

3. The method of claim 1 wherein the first tubular graft component includes a first stent attached thereto and the second tubular graft component includes a second stent attached thereto, the method further comprising securing the first and second tubular graft components within the vessel by radially expanding the first and second stents.

4. A method of placing a prosthetic graft at the bifurcation of the common iliac artery into the external and internal iliac arteries, the prosthetic graft having a first graft conduit with first and second ends and a second graft conduit attached in fluid communication with the first graft conduit, the method comprising:

providing a delivery catheter containing the prosthetic graft in a first delivery configuration;

introducing the delivery catheter into a femoral artery on the same side as the common iliac artery bifurcation;

advancing the delivery catheter to the common iliac artery bifurcation; and manipulating the delivery catheter to deploy the prosthetic graft in a second expanded configuration such that the first end of the first graft conduit is secured within the lumen of the common iliac artery, the second end of the first graft conduit is secured within the lumen of the external iliac artery and the second graft conduit is secured within the lumen of the internal iliac artery.

5. The method of claim 4 wherein the delivery catheter includes an angular control element for adjustably controlling the angle between the first and second graft conduits and wherein the method further includes manipulating the angular control element to select a desired angle between the first and second graft conduits.

6. The method of claim 4 wherein the first graft conduit includes a first stent and the second graft conduit includes a second stent, the first and second stents adapted to expand from a first delivery configuration to a second deployed configuration, the method further including securing the first end of the first graft conduit within the lumen of the common iliac artery by expanding at least a portion of the first stent to its deployed configuration and wherein the second end of the first graft conduit is secured within the lumen of the external iliac artery by expanding at least a portion of the first stent to its deployed configuration and wherein the second graft conduit is secured within the lumen of the internal iliac artery by expanding the second stent to its deployed configuration.

7. A method for repairing an abdominal aneurysm in an aorta which branches into first and second iliac arteries using a graft system having a first leg which includes first and second ends and a first bifurcated prosthetic graft having a first tubular graft portion with first and second ends and a second tubular graft portion in fluid communication with the first tubular graft portion, the first iliac artery having a bifurcation which branches into internal and external iliac arteries, the method comprising:

advancing the first leg through a first iliac artery into the aorta so that the first end of the first leg is above the aneurysm on one side thereof and the second end extends toward the bifurcation of the first iliac artery;

after the first leg has been advanced, advancing the first bifurcated prosthetic graft through the same iliac artery so that the second tubular graft portion is positioned in the internal iliac artery, the first end of the first tubular graft portion is positioned in the common iliac artery and the second end of the first graft portion is positioned in the external iliac artery; and securing the second end of the first leg to the first end of the first tubular graft portion.

8. The method of claim 7 Wherein the first leg includes an aortic stent attached to the first end of the first leg and an iliac stent attached to the second end of the first leg and wherein the first prosthetic graft includes at least one stent attached to the first tubular graft portion and a stent attached to the second tubular graft portion and wherein the method further comprises securing the first end of the first leg in the aorta by deploying the aortic stent, securing the second end by deploying the iliac stent and securing the first and second ends of the first tubular graft portion by deploying the at least one stent and securing the second tubular graft portion by securing the stent attached thereto.

9. The method of claim 7 wherein the first leg is delivered over the first guide wire prior to delivery of the first bifurcated prosthetic graft.

10. The method of claim 7 wherein the first bifurcated prosthetic graft is delivered over the first guide wire prior to delivery of the first leg.

11. The method of claim 7 further including providing a first delivery catheter for delivering the first leg and providing a second delivery catheter for delivering the first bifurcated prosthetic graft.

12. The method of claim 7 wherein the graft system includes a second leg which includes first and second ends and a second bifurcated prosthetic graft having a first tubular graft portion with first and second ends and a second tubular graft portion in fluid communication with the first tubular graft portion and wherein the method further includes:

providing a delivery system including a second guide wire;

advancing the second guide wire through the second iliac artery to a desired location in the aorta above the aneurysm;

delivering the second leg over the second guide wire so that the first end of the second leg is above the aneurysm and on one side thereof and the second end of the second leg is on the other side of the aneurysm, the second leg extending across the aneurysm;

delivering the second bifurcated prosthetic graft over the second guide wire so that the second tubular graft portion is positioned in the second internal iliac artery, the first end of the first tubular graft portion is positioned in the second common iliac artery and the second graft portion is positioned in the second external iliac artery; and securing the second end of the second leg to the first end of the first tubular graft portion of the second prosthetic graft.

13. The method of claim 7 wherein the graft system includes a second leg having first and second ends and a second bifurcated prosthetic graft having a first tubular graft portion with first and second ends and a second tubular graft portion in fluid communication with the first tubular graft portion, the second iliac artery having a bifurcation which branches into internal and external iliac arteries, the method further comprising:

advancing the second leg through the second iliac artery into the aorta so that the first end of the second leg is above the aneurysm on one side thereof and the second end of the second leg extends toward the bifurcation of the second iliac artery;

after the second leg has been advanced, advancing the second bifurcated prosthetic graft through the same iliac artery as the second leg so that the second tubular graft portion of the second bifurcated prosthetic graft is positioned in the second internal iliac artery, the first end of the first tubular graft portion is positioned in the second common iliac artery and the second end of the first graft portion is positioned in the second external iliac artery; and securing the second end of the second leg to the first end of the first tubular graft portion of the second bifurcated prosthetic graft.

14. The method of claim 4 wherein the deployment of the prosthetic graft in the second expanded configuration is performed by manipulating only the delivery catheter.

15. A method for repairing an abdominal aneurysm in an aorta which branches into first and second iliac arteries using a bifurcated graft system having a first end, first and second legs, and first and second bifurcated prosthetic grafts, each leg including first and second ends, each prosthetic graft having a first tubular graft component with first and second ends and a second tubular graft component in fluid communication with the first tubular graft component, the first and second iliac arteries each having a bifurcation which branches into first and second internal and external iliac arteries, respectively, the method comprising:

advancing the first end of the bifurcated graft system into the aorta so that the first end is above the aneurysm on one side thereof, the first leg extends toward the bifurcation of the first iliac artery and the second leg extends toward the bifurcation of the second iliac artery;

advancing the first bifurcated prosthetic graft through the first iliac artery so that the second tubular graft component of the first bifurcated prosthetic graft is positioned in the first internal iliac artery, the first end of the first tubular graft component of the first bifurcated prosthetic graft is positioned in the first common iliac artery and the second end of the first tubular graft component of the first bifurcated prosthetic graft is positioned in the first external iliac artery;

securing the second end of the first leg to the first end of the first tubular graft component of the first bifurcated prosthetic graft;

advancing the second bifurcated prosthetic graft through the second iliac artery so that the second tubular graft component of the second bifurcated prosthetic graft is positioned in the second internal iliac artery, the first end of the first tubular graft component of the second bifurcated prosthetic graft is positioned in the second common iliac artery and the second end of the first tubular graft component of the second bifurcated prosthetic graft is positioned in the second external iliac artery; and securing the second end of the second leg to the first end of the second tubular graft component of the second bifurcated prosthetic graft.

* * * * *